United States Patent [19]
Beasley et al.

[11] Patent Number: 5,389,208
[45] Date of Patent: * Feb. 14, 1995

[54] PROCESS FOR RECLAIMING AND/OR CONCENTRATING WASTE AQUEOUS SOLUTIONS OF GAS TREATING CHEMICALS

[75] Inventors: Todd Beasley, Brooks; Dwight A. Merritt, Calgary, both of Canada

[73] Assignee: Canadian Chemical Reclaiming Ltd., Brooks, Canada

[ * ] Notice: The portion of the term of this patent subsequent to Oct. 6, 2009 has been disclaimed.

[21] Appl. No.: 928,365

[22] Filed: Aug. 12, 1992

Related U.S. Application Data

[63] Continuation-in-part of Ser. No. 835,076, Feb. 18, 1992, Pat. No. 5,152,887, which is a continuation of Ser. No. 433,159, Sep. 13, 1990, abandoned.

[51] Int. Cl.[6] .............................................. B01D 3/10
[52] U.S. Cl. .......................................... 203/11; 203/14; 203/22; 203/87; 203/94; 203/100; 564/497; 423/229
[58] Field of Search .................... 203/98, 14, 94, 11, 203/42, 87, 91, 100, DIG. 9, 22; 564/497; 423/226–229; 159/46, 47.3, 29

[56] References Cited

U.S. PATENT DOCUMENTS

| | | | |
|---|---|---|---|
| 4,315,815 | 2/1982 | Gearhart | 203/40 |
| 4,770,747 | 9/1988 | Muller | 203/88 |
| 5,152,887 | 10/1992 | Beasley et al. | 203/22 |

Primary Examiner—Thomas M. Lithgow

[57] ABSTRACT

Process for reclaiming or concentrating waste aqueous solutions of gas treating chemicals, such as alkanolamines, used for removing acid components or water vapor from natural gas. The process involves heating the waste solution under a high vacuum to form a vapor and a liquid residue. The temperature and vacuum can be varied to form a vapor consisting mainly of water vapor or a vapor containing both water vapor and vaporized gas treating chemical. The vapor is subsequently condensed or passed through a wash column to produce a concentrated solution. The liquid residue is heated by passing it through a single-pass, generally co-current heater at a rate which avoids localized overheating of a liquid to a temperature above the decomposition temperature of the gas treating chemical. The heated liquid residue is then used to heat the feed waste solution by being thoroughly mixed with it, thus avoiding overheating of the feed solution. The production of corrosive elements and the use of prolonged residence times is avoided so that the apparatus may be made of carbon steel rather than more expensive stainless steel.

21 Claims, 10 Drawing Sheets

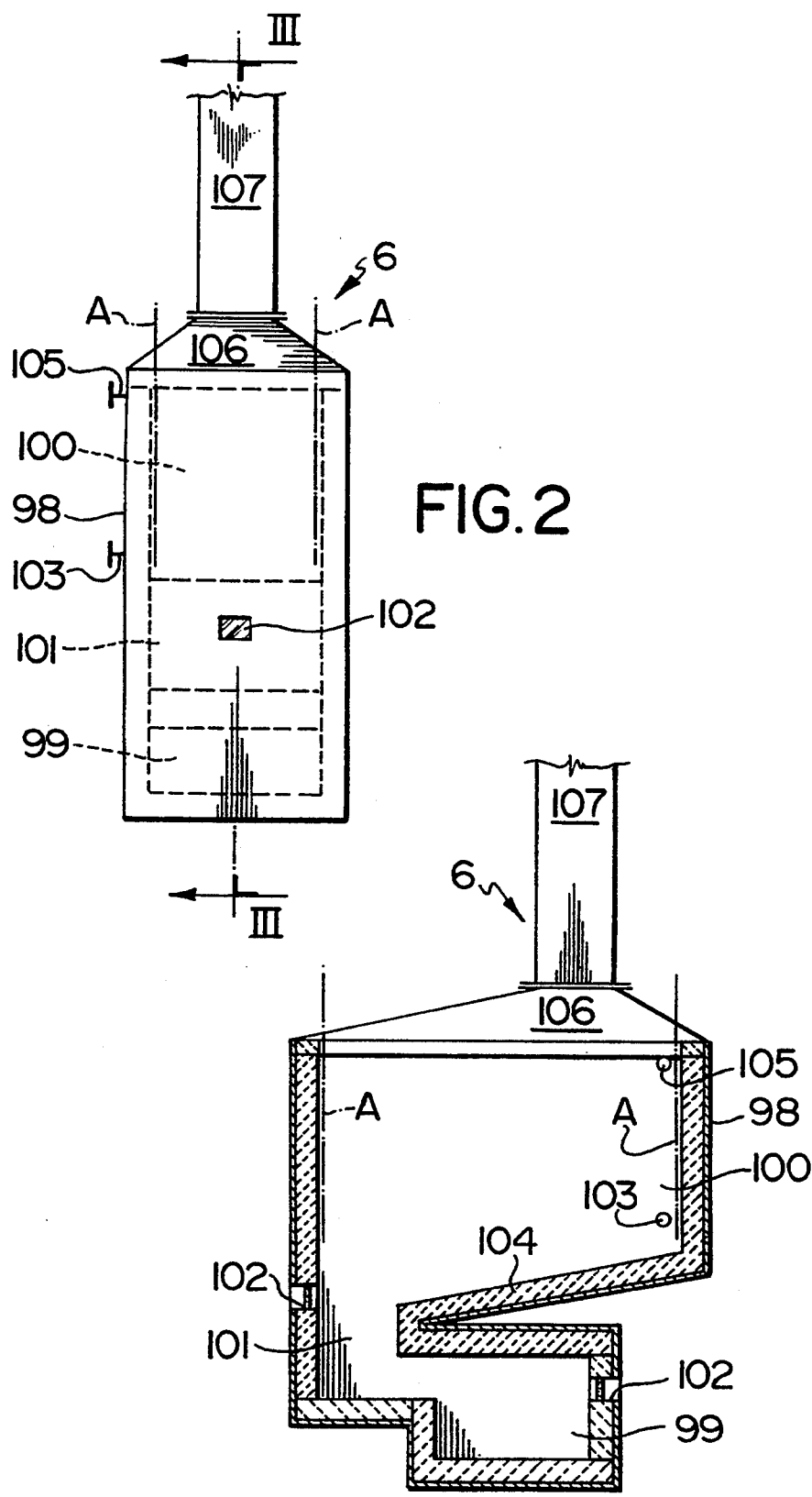

PROCESS FOR RECLAIMING AND/OR CONCENTRATING WASTE AQUEOUS SOLUTIONS OF GAS TREATING CHEMICALS

CROSS-REFERENCE TO RELATED APPLICATION

This application is a continuation-in-part of our prior application Ser. No. 07/835,076 filed on Feb. 18, 1992, now pending, which is a continuation of application Ser. No. 07/433,159 filed on Nov. 8, 1989, but having an effective filing date of Sep. 13, 1990, abandoned.

BACKGROUND OF THE INVENTION

I. FIELD OF THE INVENTION

This invention relates to a process and an apparatus for reclaiming and/or concentrating waste aqueous solutions of gas treating chemicals.

II. DISCUSSION OF THE PRIOR ART

Natural gas contains a number of acidic gaseous components, such as hydrogen sulfide and carbon dioxide, as well as water vapor, which should desirably be removed from the gas before it is transported and/or used.

These components can be removed from natural gas, and other similar gases if desired, by contacting the gas in countercurrent flow with an aqueous solution of a gas treating chemical, usually an alkanolamine such as monoethanolamine (MEA), diethanolamine (DEA) or methyl diethanolamine, or a glycol such as mono-, di- or tri-ethylene glycol, or sulfinol. The solution of the gas treating chemical efficiently absorbs the acid components or water from the natural gas. Thereafter, the solution of the gas treating chemical is regenerated by stripping the absorbed acid materials from the solution so that the solution can be recirculated and re-used for the treatment of further natural gas. This stripping operation is normally brought about by flowing the solution countercurrent through steam in a regenerator or stripper apparatus.

Over a period of time, certain contaminants build up in the gas treating solution subjected to repeated use in this way to the extent that the efficiency of removal of the acidic gaseous components is reduced or the gas treating solution becomes too viscous to pump efficiently. When this occurs, the solution is generally replaced by a fresh aqueous gas treating chemical solution. However, this gives rise to two disadvantages. Firstly, the resulting large quantities of waste solution are difficult and expensive to dispose of safely because of their content of toxic substances. Secondly, the cost of fresh gas treating chemical is quite high, so the overall cost efficiency of the process is reduced. In view of this, attempts have been made to reclaim contaminated (waste) aqueous solutions of gas treating chemicals so that they can continue to be used.

The contaminants commonly found in waste solutions of gas treating chemicals include products of the thermal degradation of the gas treating chemical, heat-stable salts, asphaltenes, light hydrocarbons, suspended solids or combinations thereof. The degradation products are high boiling nitrogen and oxygen compounds, and the heat-stable salts include sodium thiosulfate, sodium thiocyanate and sodium sulfide. In order to reclaim the waste solutions of gas treating chemicals, it would therefore be necessary to remove all such impurities from the solutions while leaving the gas treating chemical substantially intact. One way to achieve this would be to subject the waste solution to evaporation in order to liberate water vapor and vaporized treating chemical, leaving the contaminants in an unvaporized liquid residue. However, this is made difficult by the fact that all of the gas treating chemicals used for the treatment of natural gas are susceptible to decomposition at elevated temperatures. In the case of the alkanolamines, which are the preferred gas treating chemicals, any attempt to separate contaminants from the solutions by heating the solutions to temperatures above about 400° F. will result in significant thermal decomposition of the gas treating chemical itself. While the vaporization temperature of the waste solution can be reduced by carrying out the evaporation under a vacuum, it is still difficult to avoid heating parts of the solution to temperatures above 400° F. if rapid recovery of chemical from the waste solution is to be achieved.

Moreover, another problem that is encountered is that the gas treating chemicals, and particularly the alkanolamines, are corrosive and their corrosive activity increases with temperature. The corrosion problem can be serious in those parts of the equipment where temperatures are high and residence times are long.

This corrosion problem has given rise to the conventional wisdom that, when dealing with aqueous solutions of alkanolamines and other gas treating chemicals (a) the temperature should be limited to the range of 260° F. to 300° F., (b) the concentration of the alkanolamine should be limited to 30 weight percent, and (c) that stainless steel should be used for critical parts of the apparatus, i.e. those parts of the apparatus where the solution is heated and the residence times are long. For example, in "Gas Purification" by Kohl and Reisenfeld, 4th Edition, 1985, Gulf Publishing, page 121, it is stated in connection with ethanolamine gas purification that: "The authors concluded from the results of this study that all vessels and exchanger shells in the treating plant can be constructed of carbon steel. However, stainless steel, type 304, is recommended for the hottest amine exchanger pass, the boiler, the amine cooler, the amine reclaimer, and certain sections of the piping."

However, it will be appreciated that the use of stainless steel for the gas treating chemical reclaimer necessarily significantly increases the capital cost of the apparatus compared to similar apparatus made of carbon steel.

It is therefore difficult to design apparatus for reclaiming waste aqueous solutions of gas treating chemicals that can be operated both efficiently and at reasonable cost for prolonged periods of time.

A further problem is that environmental considerations are very important nowadays and gas treating chemicals, as well as their contaminants and decomposition products, are generally regarded as pollutants. It is therefore essential to ensure that any effluent from the apparatus that is intended to be discarded by dumping meets stringent anti-pollution standards.

It was stated above that there is an alternative to reclaiming waste aqueous gas treating chemical solutions, i.e. merely to discard them and to use fresh solutions, but that this gives rise to disposal problems. One way of reducing such problems would be to concentrate the waste solution by evaporating off excess water and thus reducing the quantity of hazardous material to be disposed of. Since, in such cases, there would be no intention of re-using the gas treating chemical, it might be thought that there would be no disadvantage in subjecting the chemical to temperatures above its decomposition point. This, however, is not the case because the resulting decomposition products make the solution viscous, and hence more difficult to pump, and because the higher temperatures and concentration levels of the gas treating chemical and decomposition products increase the risk of serious corrosion of the apparatus.

OBJECTS OF THE INVENTION

In view of the problems outlined above, an object of the present invention is to provide a process either for reclaiming waste aqueous solutions of gas treating chemicals or for concentrating such solutions in ways which avoid undue thermal decomposition of the gas treating chemicals.

Another object of the invention is to provide processes of this kind which can be carried out, if desired, in apparatus made of carbon steel without undue corrosion of the apparatus.

Yet another object of the invention is to provide apparatus, desirably made of carbon steel, for carrying out such processes.

SUMMARY OF THE INVENTION

The present invention makes it possible selectively to concentrate waste aqueous solutions of gas treating chemicals or to reclaim such solutions for re-use in such ways that undue decomposition of the gas treating chemical is avoided and the production of corrosive components can be minimized to such an extent that the process can be operated in apparatus made of carbon steel without causing substantial corrosion of the apparatus. Moreover, this can be achieved while maintaining a satisfactory rate of treatment of the waste solution so that the process is commercially attractive.

These advantages are achieved by maintaining the temperature of the gas treating chemical at all times below the decomposition temperature of the chemical. This can be done by partially vaporizing the solution under a high vacuum of at least 16 inches of mercury, thereby producing a vapor and a liquid residue, after heating the solution by mixing it with partially recirculated liquid residue heated to a temperature below the decomposition temperature of the chemical. The heating of the liquid residue is carried out by conveying it through tubes passing through an internal space in a heater heated by a burner producing combustion gases. To avoid localized overheating of the liquid residue, the residue is conveyed in a single pass through the internal space in a direction generally co-current to the direction of flow of the combustion gases and at such a velocity that even a thin film of the liquid residue immediately adjacent to inner surfaces of the tubes is not heated to a temperature above the decomposition temperature of the chemical. Moreover, the tubes carrying the hottest part of the liquid residue are preferably shielded from radiant heat from the burner(s) in order to reduce the risk of localized overheating even further.

Whether the solution is merely concentrated or reclaimed (purified) depends on its temperature and pressure during the evaporation step. The pressure is governed by the vacuum created in the apparatus and, while this does not vary greatly, it is usually a little less when the solution is to be concentrated than when it is to be reclaimed. The temperature of the solution when it is subjected to evaporation depends on the temperature of the feed solution, the temperature of the heated liquid residue mixed with the feed solution, and the ratio in which the heated liquid residue and feed solution are mixed, since this mixing is the only source of heating of the feed solution. If the temperature produced in this way is above the vaporization temperature of both water and the chemical at the prevailing low pressure, the generated vapor contains both water vapor and vaporized gas treating chemical. This vapour can be partially condensed to separate a purified aqueous gas treating chemical solution from residual water vapor and this solution is suitable for re-use for gas treatment. If the temperature is below the vaporization temperature of the gas treating chemical but above the vaporization temperature of water, the generated vapor is mainly water vapor and the remaining liquid residue is a concentrated aqueous solution of the gas treating chemical containing the impurities from the feed solution. This concentrated solution is removed in part (the part not recycled to the heater for heating the feed solution) and can be disposed of more easily and economically than the feed solution itself because of its reduced volume and increased concentration.

It is stated above that the process can be operated in apparatus made of carbon steel without causing substantial corrosion. By this, we mean that the rate of corrosion is low enough that it does not become detrimental to the operational lifetime of the apparatus.

BRIEF DESCRIPTION OF THE DRAWINGS

FIG. 2 is an end view of a heater used in the apparatus of FIG. 1;

FIG. 3 is a cross-sectional view taken along line III—III of FIG. 2;

DETAILED DESCRIPTION OF THE PREFERRED EMBODIMENTS

Figure 1A:
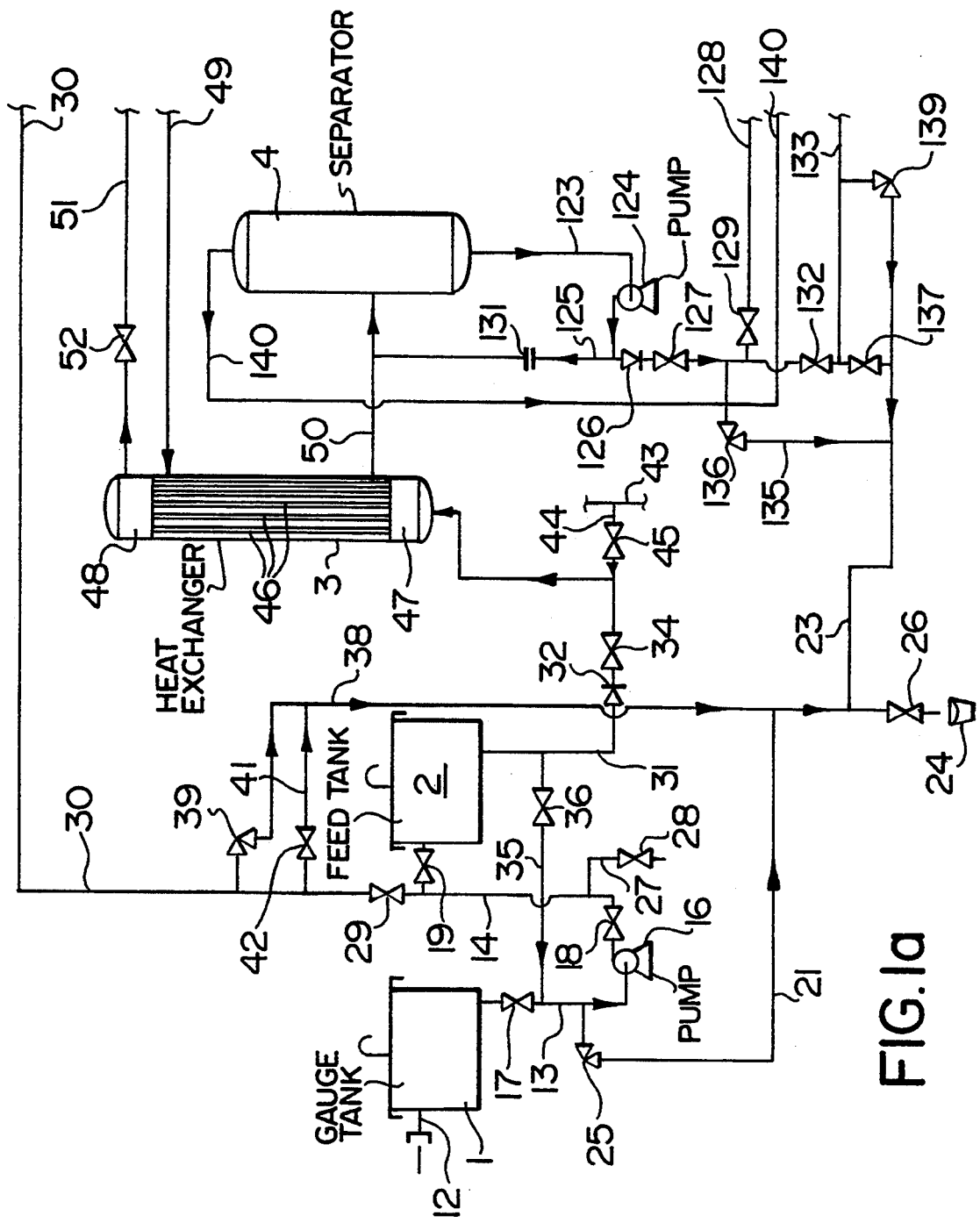
FIGS. 1a, b and c combine to form a single schematic flow diagram of a first embodiment of apparatus of the present invention.

For the sake of simplicity, the following detailed description of preferred embodiments of the method and apparatus is limited to the treatment of an aqueous diethanolamine (DEA) solution. It will however be appreciated that waste aqueous solutions of other gas treating chemicals may be reclaimed or concentrated in essentially the same way.

FIRST EMBODIMENT (RECLAIMER)

The apparatus of the first embodiment of the invention includes a gauge tank 1, a feed tank 2, a heater exchanger 3, a separator 4, a mixer 53, a still 5, a heater 6, a condenser 7, a solvent cooler 8, a filter 9 and a water cooler 10.

A waste solution of DEA is fed into the apparatus under pressure. The solution enters the gauge tank 1 through an inlet pipe 12. The tank 1 operates at atmospheric pressure and at a temperature of 40°–75° F. The tank 1 is intended to receive waste aqueous DEA feed solution from storage or from regeneration apparatus and its purpose is to allow the quantity of the solution to be measured using a liquid level gauge (not shown). The levels in the tank 1 and the following feed tank 2 are monitored. When the level in the gauge tank 1 nears the top of the tank, and the level in the feed tank 2 is low enough to receive the entire contents of the tank 1, the operator transfers the contents of the tank 1 to tank 2 through lines 13 and 14, pump 16 and valves 17, 18 and 19. While tanks 1 and 2 are operated on a batch basis in this way, the solution is fed from tank 2 on a continuous basis to the remainder of the apparatus and the downstream process operates continuously. If desired, tanks 1 and 2 may be dispensed with and feed solution feed continuously to the remainder of the apparatus.

A line 21 intersects the line 13 upstream of the pump 16 for carrying the contents of the line 13 to a drain header 23 and a receiver 24. A safety relief valve 25 is provided in the line 21, and a drain valve 26 is provided in the header 23. An outlet duct 27 with a valve 28 is provided in the line 14 downstream of the valve 18, permitting the withdrawal of samples for analysis.

During start-up operations, the valve 19 remains closed, and a valve 29 in a pipe 30 is opened to feed solution to the still 5. As noted above, feed from the tank 1 to the tank 2 is initiated manually when the operator observes that the level in the tank 2 has fallen to a level where it can accept fresh change of solution from the tank 1.

The tank 2 operates at atmospheric pressure and at a temperature of 40°–75° F. No pump is required for feeding solution downstream from the tank 2, because the other elements operate under a high vacuum of 16 to 28 inches of mercury, and flow is caused by pressure differentials between the tank 2 and such downstream elements. The feed tank 2 prevents surging, ensuring a constant flow rate in the apparatus. Flow from the tank 2 passes through line 31 and a one-way valve 32, and is controlled by a manually operated valve 34. A bypass line 35 with a valve 36 extends from the line 31 to the line 13 for draining the contents of the tank 2 through the lines 13 and 21, and the drain header 23. A line 38 with a safety relief valve 39 also connects the start-up line 30 to the drain header 23. A bypass 41 with a valve 42 connects the line 30 to the line 38 for manually effecting draining of the line 30 when the apparatus is shut down or the line 30 is not in use. The line 31 can be connected to a nitrogen purge header 43 by a line 44 and a valve 45.

Feed solution flowing from the tank 2 through the line 31 to the heat exchanger 3 enters the bottom of the latter. The feed solution enters the tube side of the heat exchanger 3, which includes a plurality of tubes 46 extending between inlet and outlet chambers 47 and 48, respectively. During passage through the tubes 46, the solution is heated by product vapors flowing countercurrent through the shell or casing of the heat exchanger 3. The product vapors flow from the still 5 via line 49 to the top end of the heat exchanger 3, and are discharged therefrom through pipe 50 to the separator 4.

The solution flowing through the tubes 46 is heated to approximately 127° F. and partially vaporized and is discharged from the outlet chamber 48 through a line 51 and a valve 52 to mixer 53. The vapors from the still 5 are cooled to approximately 133° F. during passage through the heat exchanger 3 and partially condensed. The controlled condensation of the DEA solution, facilitates the removal of water and light impurities from the solution. Moreover, the heat exchanger 3 recovers heat which otherwise would have to be added to the system, and such heat would later have to be removed by water cooling at additional expense. It should be noted, however, that heat exchanger 3 could be entirely eliminated, if desired, without changing the basic operation of this embodiment of the invention since the preheating and partial condensation thereby achieved are not essential process steps. The valve 52, which is manually actuated, controls the degree of condensation and product composition.

The partially vaporized feed solution from the heat exchanger 3 flows through the line 51 and the valve 52 to the mixer 53 where the solution is mixed with waste bottoms (unvaporized liquid residue) from the still 5. Such liquid residue is discharged through an outlet duct 60, a pump 61, a one-way valve 62, a valve 64 and a line 66 to the heater 6. A bypass 68 with a valve 69 therein is used in the event of a shutdown to drain the coil 70 in the heater 6 into the still 5. A line 72 with a solenoid operated valve 73 is connected to the line 66 and to the nitrogen purge header 43. The valve 73 is normally closed during operation of the apparatus. In the event of a power failure, a spring (not shown) in the valve opens the latter to connect the line 66 to the purge header 43, thus blowing the contents of the heater 6 into the still 5. The liquid residue passes through the heater 6 and are returned to the mixer 53 via a line 75.

During start-up, the still 5 is charged with solution entering through the line 30, a one-way valve 76 and a control valve 77. A hose connection 79 is provided in the line 30 for admitting nitrogen for purging and flushing the system. Caustic soda and anti-foaming agents, if desired, are added to the recirculated liquid residue immediately prior to the mixer 53. The caustic soda and anti-foaming agent are fed from containers 81 and 82 via lines 83 and 84, manually operated valves 85 and 86 and lines 30 and 75 into the mixer 53.

The liquid residue entering the mixer 53 is approximately 5% to 15% DEA and less than 1% water, the remainder being heavy impurities. The liquid residue is heated to no higher than 360° F. in the heater 6. The liquid residue flows to the mixer 53, which is used to heat and thus complete the vaporization of the DEA solution and vapors from the heat exchanger 3. This is effected during an extremely short residence time and with thorough mixing of the various ingredients. The mixer 53 has a tangential liquid residue entry to a main feed pipe. Mixing vanes or baffles in the main pipe may be used to ensure thorough mixing of the streams. The feed for the still 5 is changed quickly from a state with the purified gas treating chemical partially vaporized to a fully vaporized state in order to avoid degradation. As noted above, caustic soda may be added to diethanolamine feedstock to free the amine, which may be held in a heat stable salt, and to raise the pH to above 8.0 for reducing corrosion. An antifoaming agent may also be added as required to eliminate foam in the still 5. The quantity of heat and the resulting outlet temperature of the DEA from the mixer 53 are controlled by adjusting the quantity of feed to the process. This outlet temperature of the DEA from the mixer is the most important single variable in the apparatus.

The still 5 receives the mixture produced in the mixer 53 through line 87, and separates such mixture into a vapor which is returned to the heat exchanger 3 for partial condensation, and liquid residue which constitutes waste. Essentially all of the liquid residue is recirculated through the heater 6 and returned to the mixer 53. The still 5 is designed to separate vapor and liquid. The mixture from the mixer 53 is fed through a "wiping" type entrance which promotes vapor/liquid separation by centrifugal force followed by a low velocity section with sufficient residence time that promotes good vapor/liquid separation. The still 5 operates with a minimum liquid level which is normally contained in a boot 88 beneath the main body of the still casing.

The pump 61 is used to transfer liquid still reside to the heater 6, and excess liquid residue through line 90, one-way valve 91 and control valve 92 to waste drums (not shown). A vent 93 to atmosphere containing a pressure operated safety valve 94 is provided on the still 5. A hose connection 95 is provided in the line 90 for purging of the system. An outlet duct 96 with a valve 97 is also provided in the line 90 permitting the removal of samples for analysis. The pump 61 transfers liquid residue from the still 5 under vacuum to the heater 6 and to disposal, both under pressure. No control or discharge throttling is provided on the flow through the pump 61 to ensure that maximum possible flow is always maintained through the heater 6.

Figure 4:
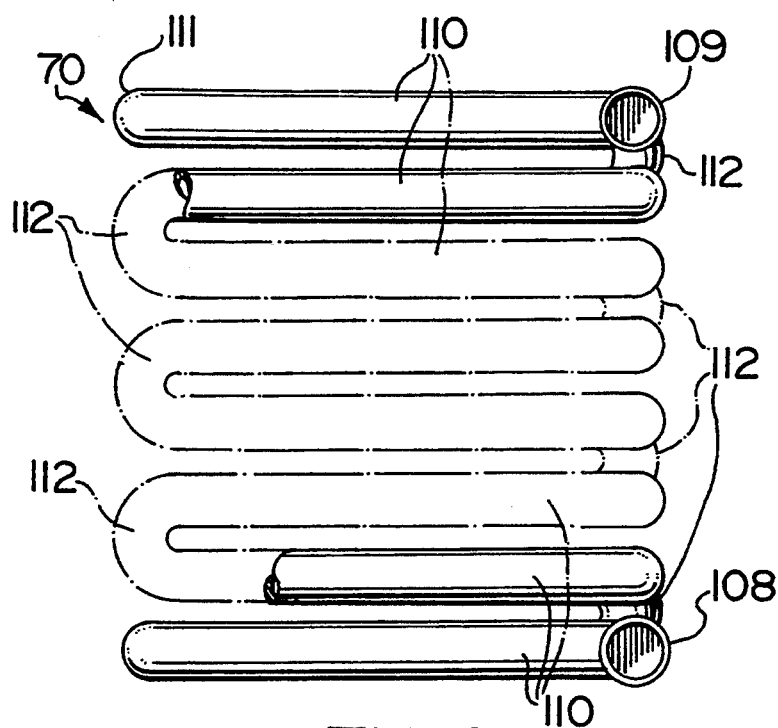
FIG. 4 is a side elevational view of a heater coil used in the heater of FIGS. 2 and 3.
Figure 5:
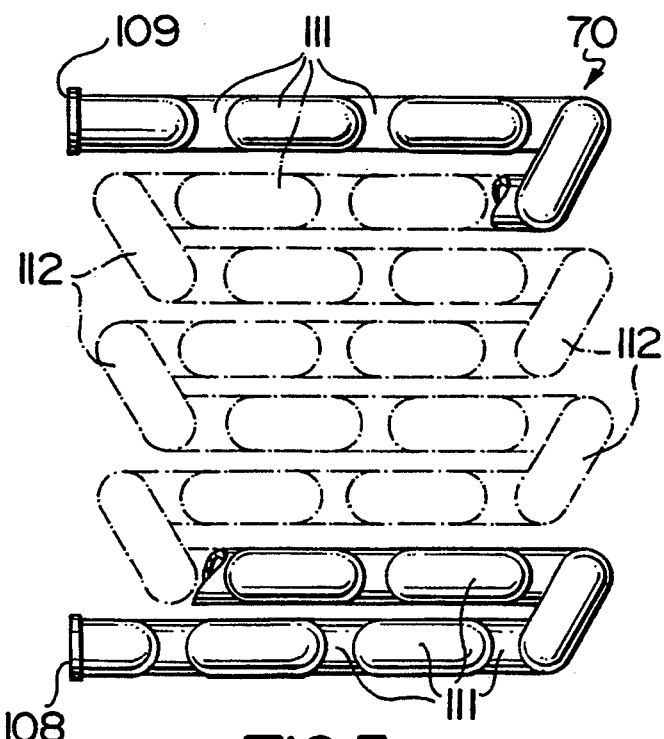
FIG. 5 is an end view of the heater coil of FIG. 4.

Referring to FIGS. 2 and 3, the heater 6 includes a steel casing 98 lined with refractory material defining a bottom section or firebox 99 for receiving a burner (not shown) and a top or coil section 100 for receiving the coil 70 (FIGS. 4 and 5). The firebox 99 and the coil section 100 are separated by a neck portion 101, so that there is no line of sight visibility between the flame in the firebox 99 and the coil 70. Sight ports 102 are provided in the firebox 99 and in the neck portion 101 of the casing. A coil inlet opening 103, i.e. and inlet to the coil 70, is provided above the inclined wall 104 of the coil section 100, and a coil outlet 105 is provided near the upwardly tapering top wall 106 of the casing. A hinged stack 107 carries flue gases from the casing 98. The stack 107 is located at the end of the casing opposite to the neck portion 101 so that hot gases must flow across the coil 70 before being exhausted from the heater 6.

The tube bundle defining the coil 70 fills most of the coil section 100 of the casing 98. The area of the tube bundle is delineated by broken lines A in FIGS. 2 and 3. The coil 70 (FIGS. 4 and 5) defines a serpentine path through the top section 100 of the casing 98 from a bottom inlet end 108 to a top outlet end 109. The coil 70 includes a plurality of straight sections 110 interconnected at the ends by 180° return bends 111. At the end of each horizontal row of sections 110 a 180° return bend 112 rises to the next superjacent row of sections 110.

The heater 6 heats the liquid residue in a one-pass flow from an inlet temperature of 330° F. to an outlet temperature of 360° F. There is no other heat source for such liquid reside. At the heater outlet, less than 1% of the feed is vaporized. Thus, the walls of the heater tubes are continuously covered with liquid. The heater firebox 99 receives natural gas or oil from a source thereof via line 114, solenoid valve 115 and control valve 116. The firebox 99 also acts as a combustion site for waste gases fed from the bottom of condenser 7 via line 117, a vacuum pump 118, line 119, one-way valve 120, solenoid-operated valve 121 and flame arrester 122. The heater 6 provides the heat input for the apparatus and burns waste gases from the vacuum pump 118, converting the gases to less noxious substances. The products of combustion are discharged via the stack 107.

The design and operation of the heater 6 are important in order to prevent degradation of the DEA product. The use of a vacuum in the still 5 permits vaporization of the DEA at a temperature below that at which decomposition starts. However, since the liquid residue contain DEA, care must be taken to ensure that the liquid reside is not subjected to a temperature of 400° F. or more at any point in the heater 6. In fact, this temperature limitation not only refers to the bulk fluid temperature within the heater coils, i.e. the temperature of the fluid at the centreline of the tubing, but also the temperature immediately adjacent to the walls of the tubing, ie. the temperature of a thin film of fluid adjacent to the inner tube walls. Since the heat enters the fluid through the tube walls, this latter thin film temperature is always higher than the bulk fluid temperature, and care has to be taken to ensure that the critical temperature is not exceeded. This is achieved in the present invention by (a) passing the liquid reside through the heater tubing at a suitably high rate of flow (at least six feet per second and more preferably 7 to 10) so that the residence time close to any "hot spots" in the tubing is kept low, (b) passing the liquid reside through the tubing of the heater in a single pass to avoid possible problems of flow distribution between passes and to ensure that all parts of the tubing receive a positive full flow of circulated material, which avoids points at which the fluid may have a low velocity which may result in decomposition, and (c) passing the liquid reside through the tubing in a direction co-current to the combustion gases so that the liquid residue at their coolest temperature enter the tubing where the combustion gases are at their highest temperature and then exits the tubing from the top of the heater where the combustion gases are at their lowest temperature. The liquid reside at their highest bulk temperature are thus exposed only to the combustion gases at their lowest temperature, further reducing the risk of overheating by ensuring that the film temperature is raised by only a minimum above the bulk temperature.

By taking these measures, not only can decomposition of the DEA in the liquid residue be avoided, but the corrosiveness of the liquid residue can be minimized, since corrosiveness increases with temperature. It is therefore possible to use inexpensive carbon steel for the heater tubes rather than expensive stainless steel.

The quantity of bottom waste flowing to the heater 6 and the velocity of waste liquid in the heater tubes also ensure that outlet vaporization is less than 1%, and that the residence time of waste liquid in the heater 6 is from 30 to 60 seconds. There is no direct heat transfer from the burner flame to the waste liquid in the heater 6, heating being effected by convection only. Thus, heat transfer is limited to approximately 5,000 BTU/h/ft$^2$. There is no direct flame contact with the heater tubes.

The product vapor separated from the liquid reside in the still 5 is returned to the product separator 4 (FIG. 1a) via the line 49, the heat exchanger 3 and the line 50. Thus, partially condensed DEA (the product) from the heat exchanger 3 is fed to the separator 4. The liquid, which is the purified product, is separated from the vapor, which is essentially all water vapor. The separated liquid is discharged through a line 123 and pump 124 to a line 125 and through a one-way valve 126, a control valve 127, a line 128 and a valve 129 for further treatment in the solvent cooler 8 (FIG. 1c) as described hereinafter in greater detail. The line 50 is also connected to the line 125 through a restriction orifice 131, which passes minimum flow for pump 21 through the line 125. Start-up condensate flows through the valves 126 and 127, a valve 132 and a line 133 to product water storage (not shown). A line 135 containing a safety relief valve 136 connects the line 125 to the drain header 23. The line 125 is also connected through a valve 137 downstream of the valve 132 and the line 133 to the drain header 23. The line 133 is also connected by a safety valve 139 to the drain header 23. The water vapor discharged from the top of the separator 4 is fed through line 140 to the top of the condenser 7 (FIG. 1c).

The product may be discharged without further treatment or may be pumped to the cooler 8 under sufficient pressure to deliver the product to the user. If the cooler is used, the warm product at 130° F. flows to the outer tube of the coaxial tube, countercurrent flow cooler 8. The cooler 8 reduces the temperature of the product to a level which is safer to handle and deliver to the user. The cooled product then passes through line 142 and, if desired, may be passed through valve 143 into the filter 9, or directly through a valve 145 to a product discharge line 146. If the filter is used, the product is discharged from the filter 9 through a line 148 and a valve 149 to the line 146. Samples for analysis can be removed from the line 146 through valve 150.

Warm vapor and non-condensibles from the separator 4 enter the top of the condenser 7 via line 140 at a temperature of approximately 130° F. These substances flow through tubes 152, cooling to approximately 90° F. and condensing. Cooling water for the condenser 7 enters the bottom of the condenser casing through a line 153, valve 154, line 156, pump 157 and line 158 connected to a reservoir or tank 160. The tank 160, lines 156 and 158, and pump 157 also supply the cooler 8 via valve 161 and line 162. A bypass 164 containing a valve 165 extends between the line 162 and the tank 160. Water passing through the condenser 7 is discharged through a line 167 and fed to the water cooler 10. The water cooler 10 includes a fan 168 and an inlet tube 170 containing spray orifices. The cooler 10 is connected by line 171 to the water tank 160. A heater 173 in the tank 160 is used to prevent freezing during start-up and shut down operations.

Figure 1B:
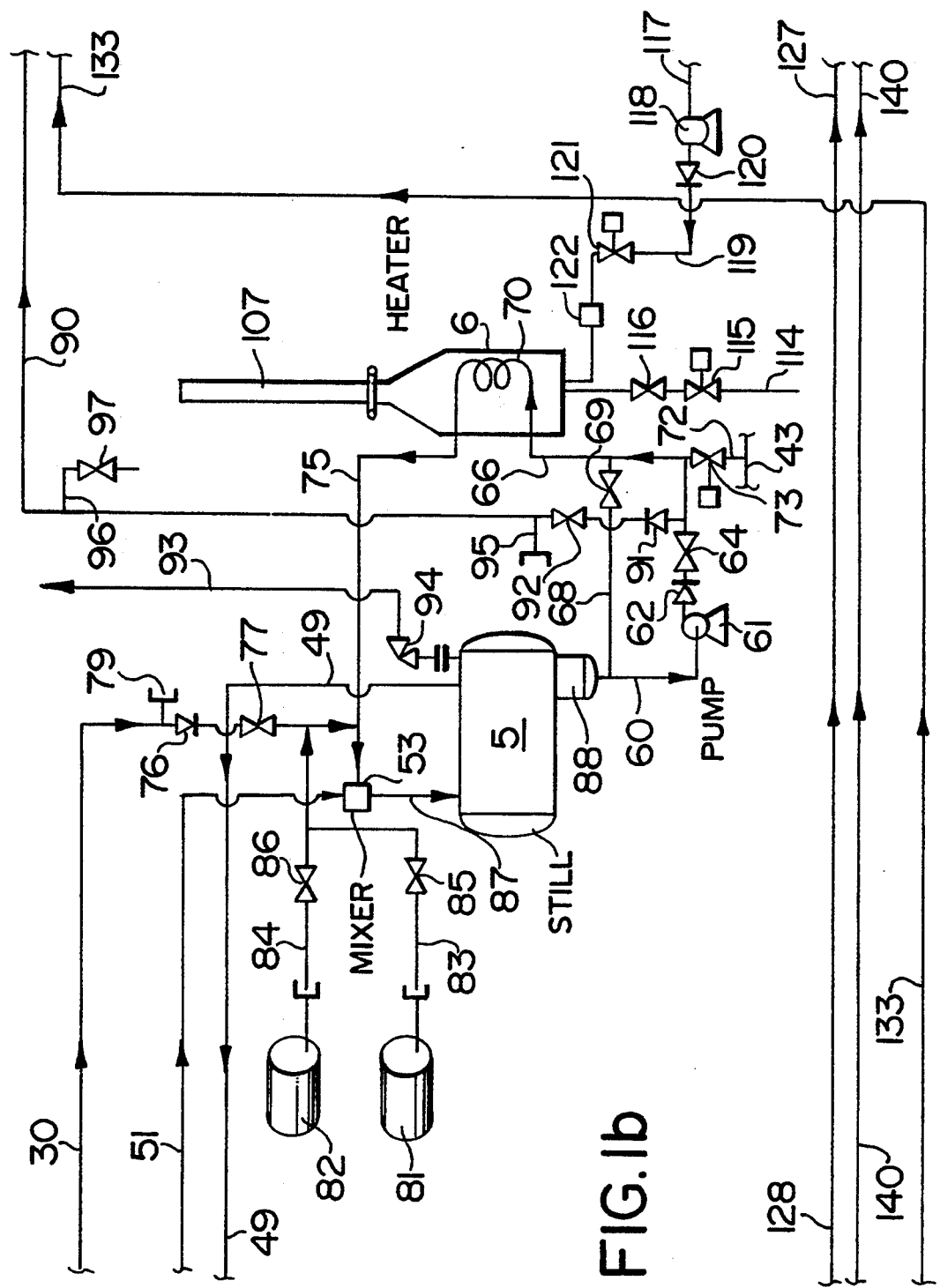
Figure 1C:
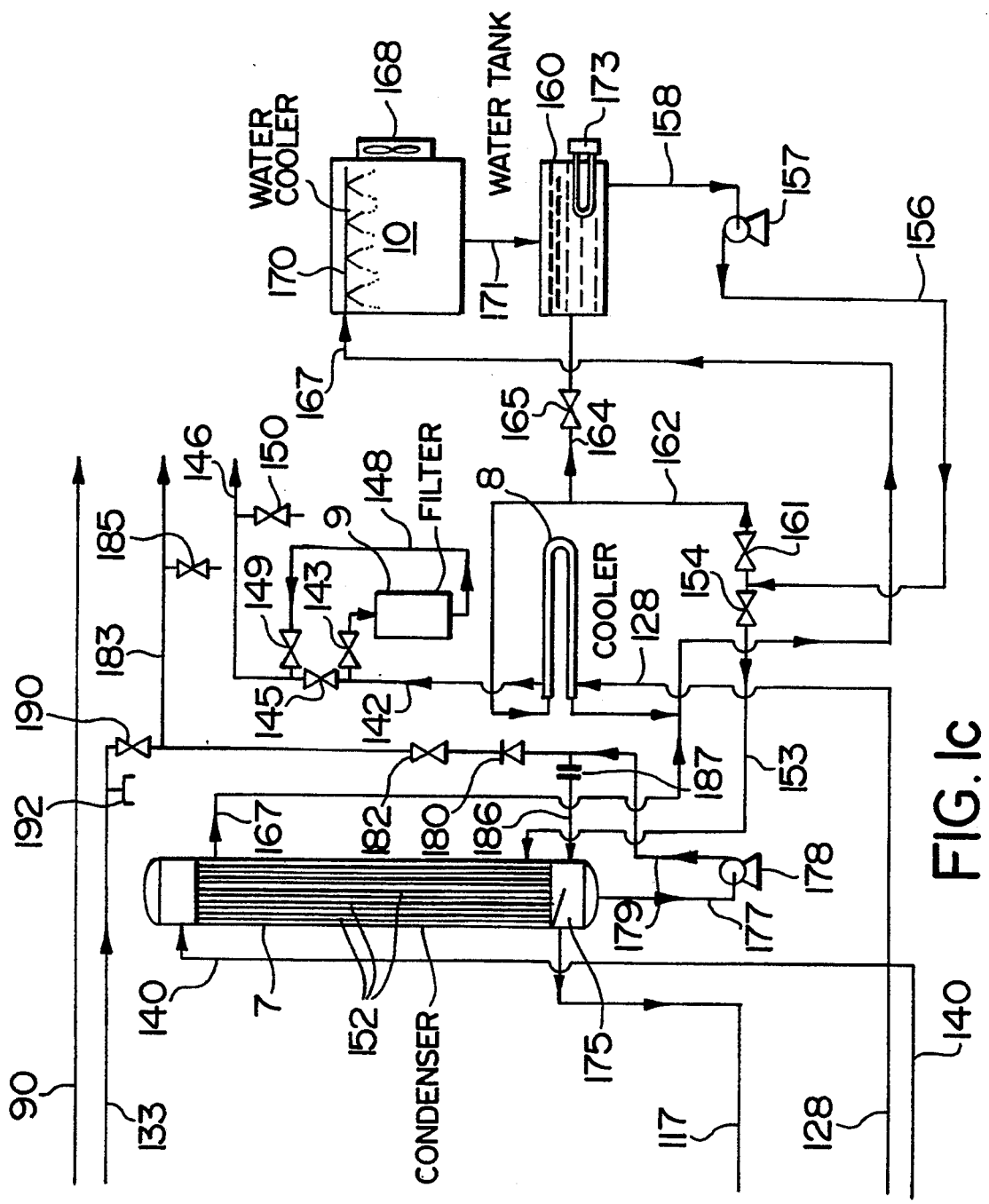

Non-condensible gases are separated from condensed water in the bottom head 175 of the condenser 7, and flow through line 117 to the vacuum pump 118 (FIG. 1b). The condensed water, after separation in the bottom head 175 flows through line 177, condensate pump 178, line 179, one-way valve 180 and control valve 182 to a discharge line 183, which is used to discharge the condensate to disposal. A sample can be removed from the discharge line 183 through valve 185 for analysis. The line 179 is connected to the bottom head 175 of the condenser 7 by a line 186 and a restriction orifice 187, which ensures a minimum flow through the pump 178 at all times and recirculation to suction.

During start-up, start-up condensate is passed through line 133 from line 123 and the separator 4 through a valve 190 into the downstream end of the condenser system. A hose connection 192 is provided in the line 133 for connecting such line to a source of nitrogen for purging and flushing.

The condenser 7 cools and condenses water already removed from the feed, and separates and removes non-condensible gases from the condensate. The liquid residue head 175 acts as a vapor/liquid separator. Any air leaking into the vacuum system or gases dissolved in the feed are present at the outlet of the condenser as non-condensibles. The removal of such air and gases through the line 106 is the mechanism by which a high vacuum can be maintained in a major part of the apparatus. In this connection, it will be noted that there is a clear path by which to maintain a vacuum between the condenser 7 via line 140 to the separator 4, via line 50 to the heat exchanger 3, via line 49 to the still 5, via line 87 to the mixer 53, and via line 51 and the tubes 46 of the heat exchanger 3.

The non-condensible gases from the condenser 7 flow to the vacuum pump 118 where the gases are compressed from a vacuum of approximately 28″ of mercury to a slight positive pressure above atmospheric. The discharge from the vacuum pump 118 flows through the flame arrester 123 to a special burner in the heater 6 where the gases are completely burned and discharged through the stack 107 to the atmosphere.

Briefly, during normal operation and following start-up the process utilizing the above-described apparatus includes the steps of charging the apparatus with chemical to be reclaimed via the gauge tank 1 and the feed tank 2, preheatinq the chemical in the heat exchanger 3, feeding the partially vaporized chemical through line 51 to be mixed, if necessary, with caustic soda and anti-foaming agent and then to the mixer 53 where it is mixed and further vaporized with heated liquid residue from the still 5 and the heater 6, and mixture thus produced in the still 5, returning the vapor from the still to the heat exchanger 3, and separating reclaimed chemical (product) in the separator 4. The residence time in the mixer 53, i.e. the mixing time is less than one second. An important step in the process is the heating of the liquid residue from the still in the heater 6, and using the thus heated liquid residue to effect separation in the still 5 in a high vacuum and at a temperature of less than 400° F. to avoid decomposition. There is no direct or other heating of the still 5 or the contents thereof. It is worth noting that the liquid residue from the still always contain 5–15% of feed chemical to ensure fluidity of such liquid residue.

As noted above, an advantage of the process is that it can be carried out in apparatus made largely or wholly of carbon steel rather than stainless steel with a large consequent reduction of capital costs and without significant corrosion. While certain pre-fabricated components such as valve seats and mixer vanes would normally still be made of stainless steel in the apparatus of the present invention, inexpensive carbon steel could be used for all piping, heat exchangers, condensers and, most importantly, for the still 5 and heater 6.

SECOND EMBODIMENT (CONCENTRATOR OR RECLAIMER)

A preferred second apparatus according to the present invention is shown in FIGS. 6 to 11. In these Figures, for the sake of simplicity, elements similar or identical to those in the previous figures have the same identifying reference numerals.

Figure 6A:
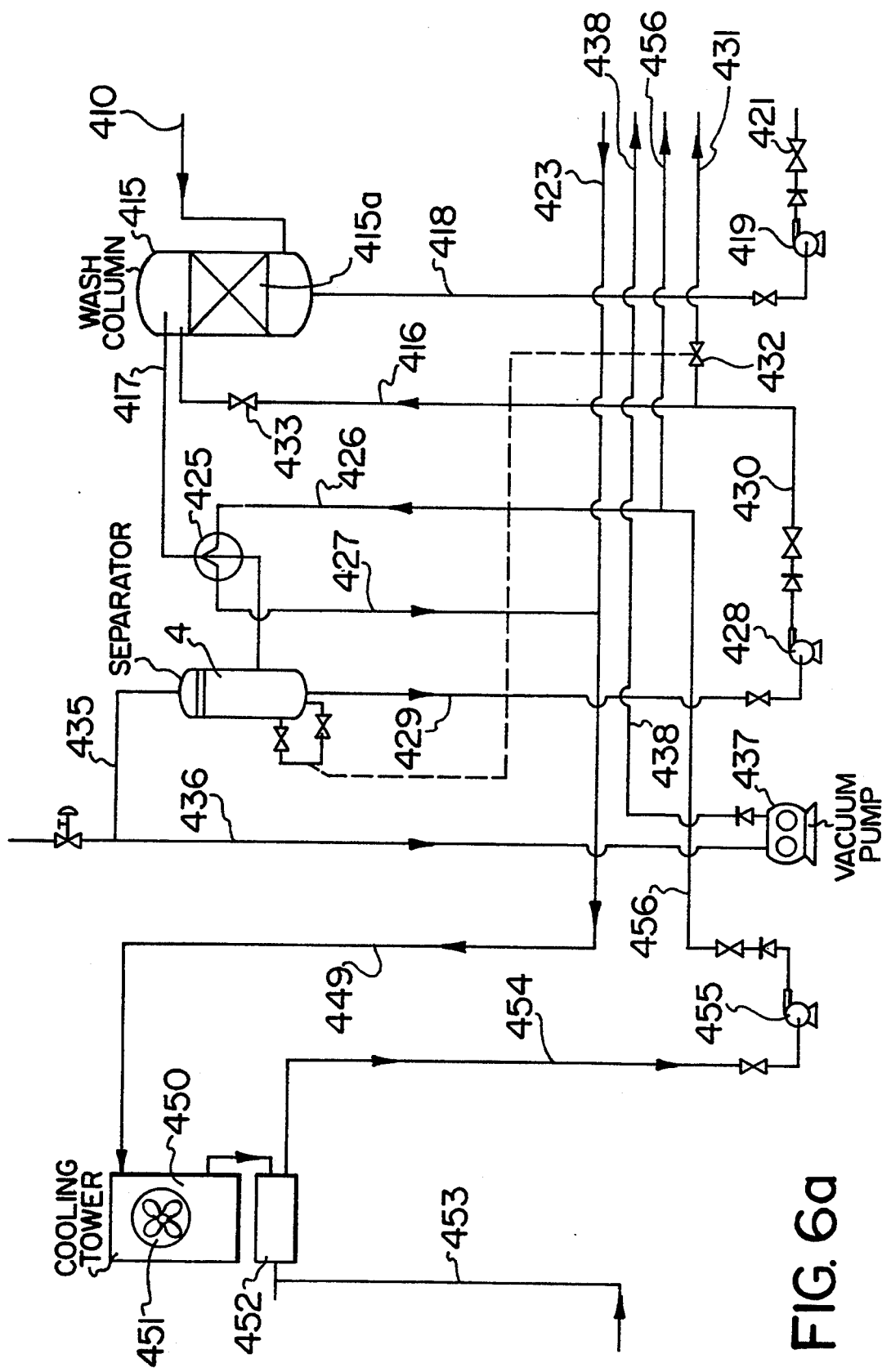
FIGS. 6(a) and 6(b) combine to form a single schematic flow diagram of a second preferred embodiment of the apparatus of the present invention.
Figure 6B:
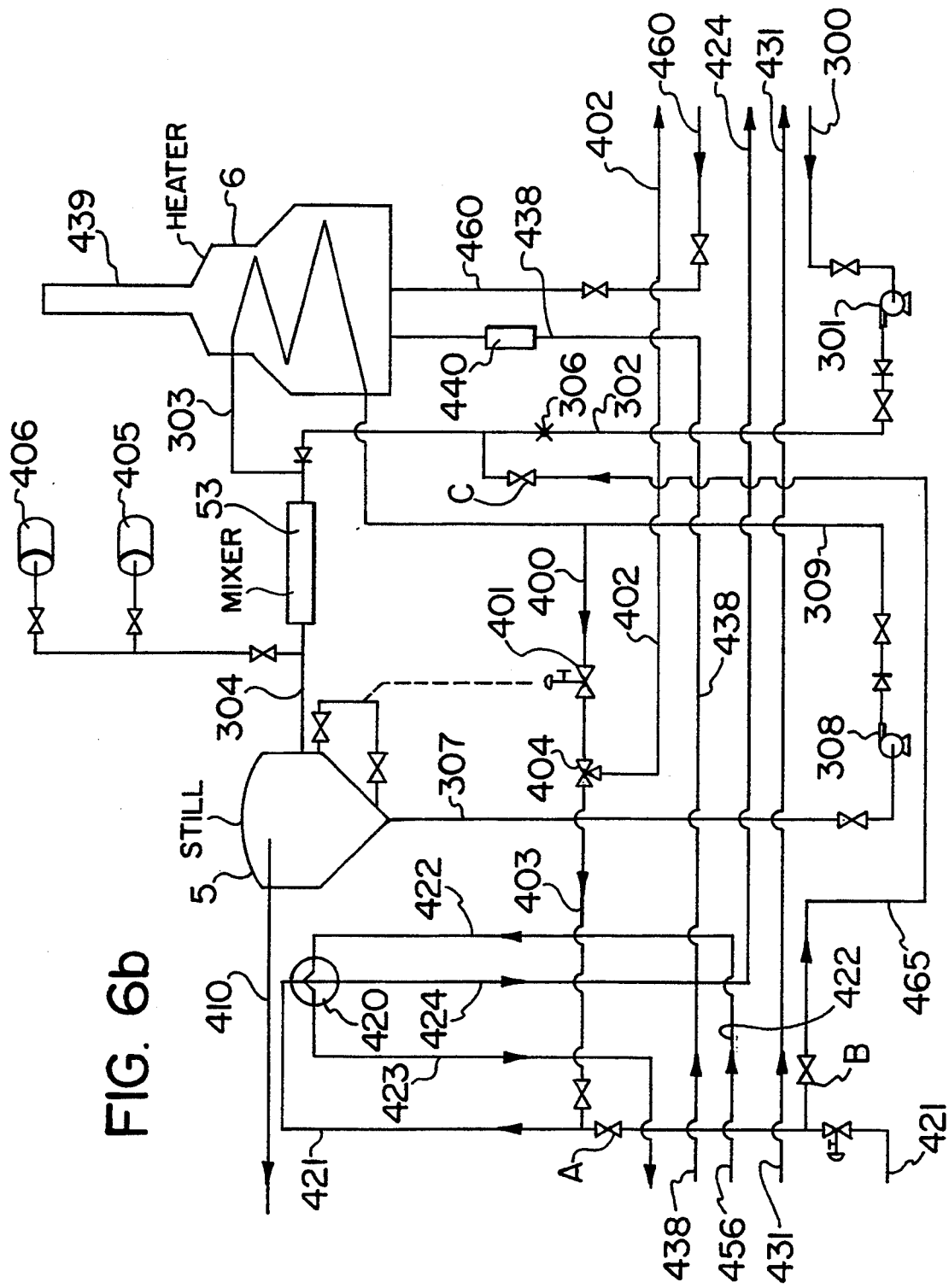
Figure 7:
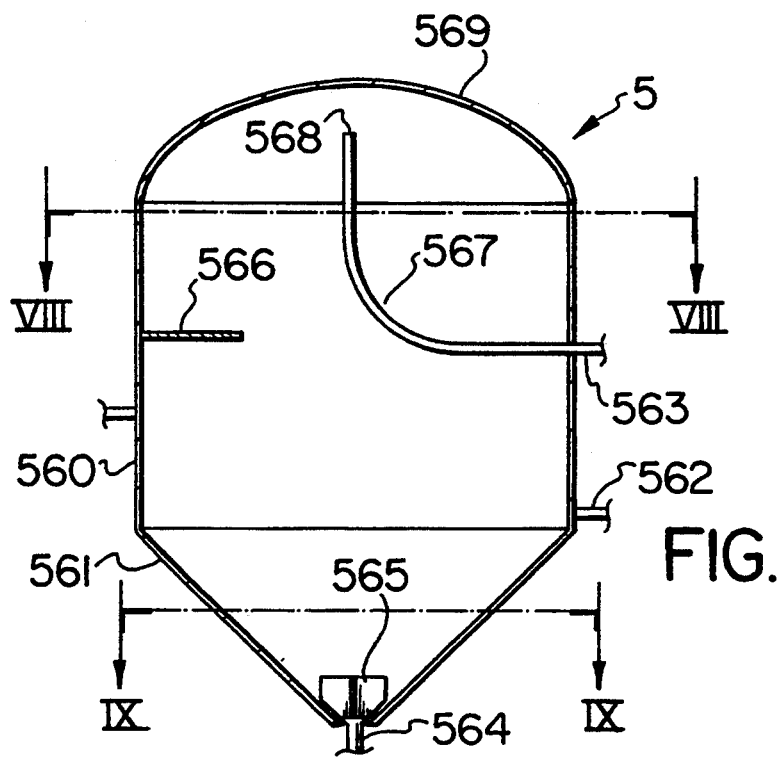
FIG. 7 is a vertical cross-section of a still used in the apparatus of FIG. 6.
Figure 8:
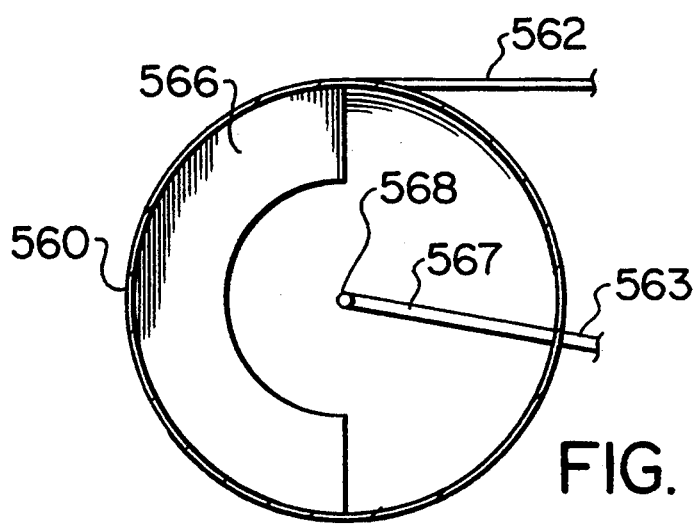
FIG. 8 is a cross-section of the still of FIG. 7 taken on the line VIII—VIII of FIG. 7.
Figure 9:
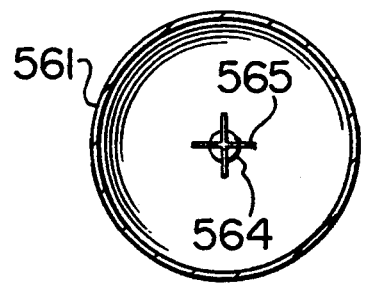
FIG. 9 is a cross-section of the still of FIG. 7 taken on the line IX—IX of FIG. 7.

The apparatus shown in FIGS. 6(a) and 6(b) is similar in important ways to that shown in FIGS. 1(a), 1(b) and 1(c) but differs in several material respects. Moreover, the apparatus is capable of being used for concentrating solutions of waste gas treating chemicals as well as reclaiming them for re-use. Solutions concentrated in this way cannot be re-used for removing impurities from natural gas because they still contain the impurities which made them ineffective for this purpose in the first place, but the concentrated solutions can be disposed of more easily and inexpensively than the dilute waste aqueous solutions forming the feed to the apparatus.

The operation of the apparatus as a concentrator will be described first.

FIRST CONCENTRATOR MODE OF OPERATION

A waste aqueous feed solution of the gas treating chemical normally having a temperature of about 80° F. is drawn into the apparatus via inlet pipe 300 (FIG. 6(b)) by charge pump 301 and is fed to mixer 53 via pipe 302, mixer 53 being a static mixer having fixed internal vanes. Prior to entering the mixer 53, however, the feed solution is mixed with heated liquid from heater 6 at the junction of pipes 302 and 303. The heated liquid is thoroughly mixed with the feed solution in the mixer 53 and heats the feed solution without raising its temperature above the decomposition temperature of the gas treating chemical (400° F.), as in the first embodiment described earlier.

The heated mixed solution from the mixer 53 is conveyed via pipe 304 to still 5. The still differs in design from that shown in FIGS. 1(a), 1(b) and 1(c) and is more fully described below with reference to FIGS. 7 to 9. In the still 5, which operates under a vacuum of 16 to 28 inches of mercury and preferably at 23–24 inches of mercury when the apparatus is being operated as a concentrator, the mixed solution from the mixer 53 is separated into a vapor component, which is mainly water vapor, and a concentrated, impurity-containing, solution of the gas treating chemical forming a liquid residue. This differs from the separation taking place in still 5 of the first embodiment where a vapor comprising water and gas treating chemical is produced and separated from a waste liquid residue containing some gas treating chemical and impurities. The reason for this difference is that the mixture from mixer 53 in this embodiment, when operated as a concentrator, is at a temperature below the boiling point of the gas treating chemical at the indicated pressure, but above the boiling point of water. In the first embodiment, the temperature was above the boiling point of both the gas treating chemical and water at the prevailing pressure. The temperature is of course governed by the respective temperatures, pressures and rates of flow of the liquids passing through pipes 302 and 303. Since the temperatures of these liquids remain substantially constant, the temperature of the mixture entering still 5 is controlled largely by the position of valve 306 in pipe 302.

The unvaporized liquid residue of the gas treating chemical exits the still 5 through pipe 307 and is circulated by recirculation pump 308 to heater 6 via pipe 309 where it is heated and delivered to pipe 303. The heater 6 may be the same as the heater used in the first embodiment, but is preferably a modified heater of the kind described in more detail below with reference to FIGS. 10 and 11.

As the process proceeds, the amount of liquid residue from still 5 continuously increases and the excess is diverted through pipe 400 according to the position of control valve 401, this valve being controlled automatically (as indicated by the dashed line) according to the level of liquid residue in the still 5 in order to keep the level between minimum and maximum limits. The liquid residue passes through three-way gate valve 404 to pipe 403 and from there to pipe 421. The subsequent flow from pipe 421 will be explained more fully later.

As in the first embodiment described earlier, caustic soda solution (preferably a 20% solution) from tank 405 and a solution of an anti-foaming agent from tank 406 may be added to the mixture introduced into the still 5 from mixer 53, if desired.

Vapor produced in still 5 is removed via pipe 410, which communicates with the upper part of the still, and is conveyed to a lower section of a wash column 415 containing a packing medium 416, preferably Glitsch structured packing or equivalent. Condensate (liquid water) is introduced into an upper part of the wash column 415 from pipe 416 and trickles downwardly through the packed medium 415a in contact with the rising vapor from still 5. This creates a multi-stage refluxing action between the condensate and the vapor, which has the effect of condensing any small amount of gas treating chemical vapor contained in the vapor from the still and dissolving it in the solution draining to the bottom of the wash column 415. Consequently, vapor emerging at the top of the wash column is virtually pure water vapor, which then exits the wash column 415 through pipe 417. The solution collecting at the bottom of the wash column exits via pipe 418 and is pumped by pump 419 to cooler 420 via pipe 421, valve A being open and valves B and C (in pipe 465) being closed. In cooler 420, the solution is cooled by cooling water conveyed to and from the cooler via pipes 422 and 423, respectively.

Prior to entering the cooler 420, however, the solution is mixed with the excess liquid residue, i.e. concentrated gas treating chemical solution, from pipe 403 as explained above.

The cooled solution leaving cooler 420 is discharged from the apparatus via pipe 424 for disposal as partially concentrated waste.

SECOND CONCENTRATOR MODE OF OPERATION

As an alternative to the above flow pattern, valve A may be closed and valves B and C opened. This means that the dilute solution from wash column 415 passes through pipe 418 to pipe 421, but is diverted via pipe 465 to mix with the waste solution feed in pipe 302 and is thus recirculated to the mixer 53 and still 5. Cooler 420 now receives only excess liquid residue from still 5 via pipes 307, 309, 400, 403 and the part of line 421 downstream of valve A. This allows an even more concentrated solution to be discharged through pipe 424 without requiring higher temperatures in the still 5.

GENERAL CONCENTRATOR OPERATION IN BOTH MODES

The water vapor leaving the wash column 415 via pipe 417 passes through a cooler 425, supplied with cooling water via pipes 426 and 427, to cool the vapor to a temperature below its boiling point. The cooled vapor/condensate then passes to vapor/liquid separator 4 which collects the condensate in the lower section of the separator, from where it is extracted by condensate pump 428 via pipe 429. The condensate passes through pipe 430 and is discharged from the apparatus via pipe 431 as virtually pure water which can be discharged without risk of causing pollution. The discharge of the condensate is automatically controlled by control valve 432 which is operated automatically (as indicated by the dashed line) according to the level of condensate in the separator 4 in order to ensure that the condensate in separator 4 is always maintained between minimum and maximum levels. However, pipe 416 communicates with pipe 430 so that some of the condensate is diverted and delivered to wash column 415, as explained above, according to the position of gate valve 433.

Gases remaining uncondensed in separator 4, which may include uncondensed water vapor, decomposition gases or air which has leaked into the apparatus, are withdrawn from the top of the separator via pipes 435 and 436 under the action of vacuum pump 437, which provides the vacuum for the entire apparatus. Since the uncondensed gases may include noxious substances, they are conveyed to heater 6 via pipe 438 for destruction of any chemical components within the flames from burners in the heater and are then discharged through heater stack 439. A flame arrester 440 is provided in pipe 438 near the heater 6 to prevent backdraft and explosion in the pipe.

The cooling water used for heat extraction in coolers 420 and 425 is conveyed from the coolers via pipes 423 and 427, respectively, and pipe 449 to cooling tower 450 where the heat is exchanged with cooling air circulated over cooling tubes by fan 451. The cooled water is collected in surge tank 452 and any shortfall is made up by water from pipe 453. The cooling water from the surge tank is extracted by through pipe 454 by cooling water pump 455 and delivered via pipe 456 to the coolers 425 and 420 via pipes 426 and 422, respectively.

A fuel, such as natural gas or oil, is fed to heater 6 via pipe 460 for the operation of burners within the heater to effect heating of the concentrated solution from the still 5 as explained above.

When the apparatus is operated as a concentrator, the input waste aqueous solution of gas treating chemical is separated into a concentrated, impurity-containing solution discharged through pipe 424 and substantially pure water discharged through pipe 431.

The pure water discharged from the apparatus meets current standards regarding C.O.D. and B.O.D. and can thus be discharged into a river, lake or sea without causing pollution, and the concentrated solution can be disposed of as a hazardous chemical.

RECLAIMER MODE OF OPERATION

When the apparatus of FIGS. 6(a) and 6(b) is to be used for reclaiming waste aqueous solutions of gas treating chemicals rather than concentrating them in the manner described above, the temperature of the liquids entering the still 5 from the mixer 53 is raised above the boiling point of both the gas treating chemical and water at the pressure within the still (which is preferably decreased to a vacuum of about 28 inches of mercury) by reducing the input rate of the feed solution through pipes 300 and 302. The vapor leaving the still via pipe 410 then contains both water and gas treating chemical. In the wash column 415, the gas treating chemical is separated from much of the remaining water vapor and a fairly concentrated purified solution of gas treating chemical emerges via pipe 418 and is pumped by pump 419 to line 421 for cooling in cooler 420 and discharge through line 424.

The liquid residue in the still 5 contains impurities and a small amount of gas treating chemical to decrease the viscosity, as in the first embodiment described earlier. Since the amount of liquid produced in the still is reduced, only a small amount is removed through pipe 400. Valve 404 is positioned so that all of this residue enters pipe 402 rather than 403 and is discharged from the apparatus. The apparatus functions in essentially the same way as the apparatus of FIGS. 1(a), 1(b) and 1(c), except for the lack of preheating of the feed solution, so further detailed description is believed to be unnecessary.

As mentioned above, in the apparatus shown in FIGS. 6(a) and 6(b), the still 5 has been modified in design compared to the still shown in FIG. 1, although the function remains essentially the same. The modified still is shown in greater detail in FIGS. 7, 8 and 9.

The still 5, instead of being in the form of a horizontally-arranged cylinder provided with a liquid reservoir or boot 88, is in the form of a vertically-arranged cylinder 560 provided with an inwardly tapering conical lower section 561 providing an inwardly and downwardly tapering inner conical surface area. The still has a tangential inlet 562 for receiving mixed feed solution and heated liquid from mixer 53 via pipe 304. The still is also provided with a vapor outlet 563 for connection to pipe 410 and a liquid outlet 564 for connection to pipe 307.

The tangential arrangement of inlet 562 causes the mixed feed solution and heated liquid from mixer 53 to follow a generally spiral path around the inner surface of the cylindrical and conical sections 560 and 561 as gravity attracts the liquid towards the liquid residue outlet 564. This helps to permit the mixture to separate quickly into vapor and liquid components by ensuring that the mixture is "wiped" by centrifugal force over a considerable area of the inner still wall.

The conical lower section 561 collects the unvaporized liquid residue around the liquid outlet 564 and, because of the conical design, provides a minimum of liquid volume or residence time within the still, thus minimizing the possibility of degradation or settling of solids that may be present, while allowing a sufficient workable liquid level for control. Moreover, the tangential positioning of the inlet 562 and the conical design of the lower section 561 ensures that the entering liquid flows at high velocities in a circular and downward direction. This down-flowing liquid has a flow pattern which ensures that any solids present are washed down to the outlet 564 and thus avoid the potential adhesion and accumulation of such solids on the internal walls of the still.

At the extreme lower end of the conical section 561, a vortex breaker element 565 is provided immediately ahead of the outlet 564. This element is formed by a pair of flat plates intersecting each other at right angles. These plates prevent circular motion of the fluid adjacent to the outlet to prevent gaseous components from being drawn into the outlet tubing 307 which is the suction of the circulating pump 308.

Towards the upper end of the still 5, a semi-circular baffle plate 566 projects from the inner cylindrical wall of the still. This prevents the liquid in the mixture from inlet 562 from moving to the upper part of the still. Vapor outlet 563 is connected to an internal pipe 567 having an inlet 568 facing upper end wall 569 of the still. This arrangement forces vapor separated from the mixture in the lower part of the still to follow a reverse flow path at the inlet 568, causing any liquid entrained in the vapor to impact and adhere to the inner surface of the wall 569, thus effectively removing the liquid from the vapor and allowing it to return eventually to the lower outlet 564.

It should be noted that, although the still 5 is shown as part of the apparatus of the second embodiment, it could also be used in the apparatus of the first embodiment.

Figure 10:
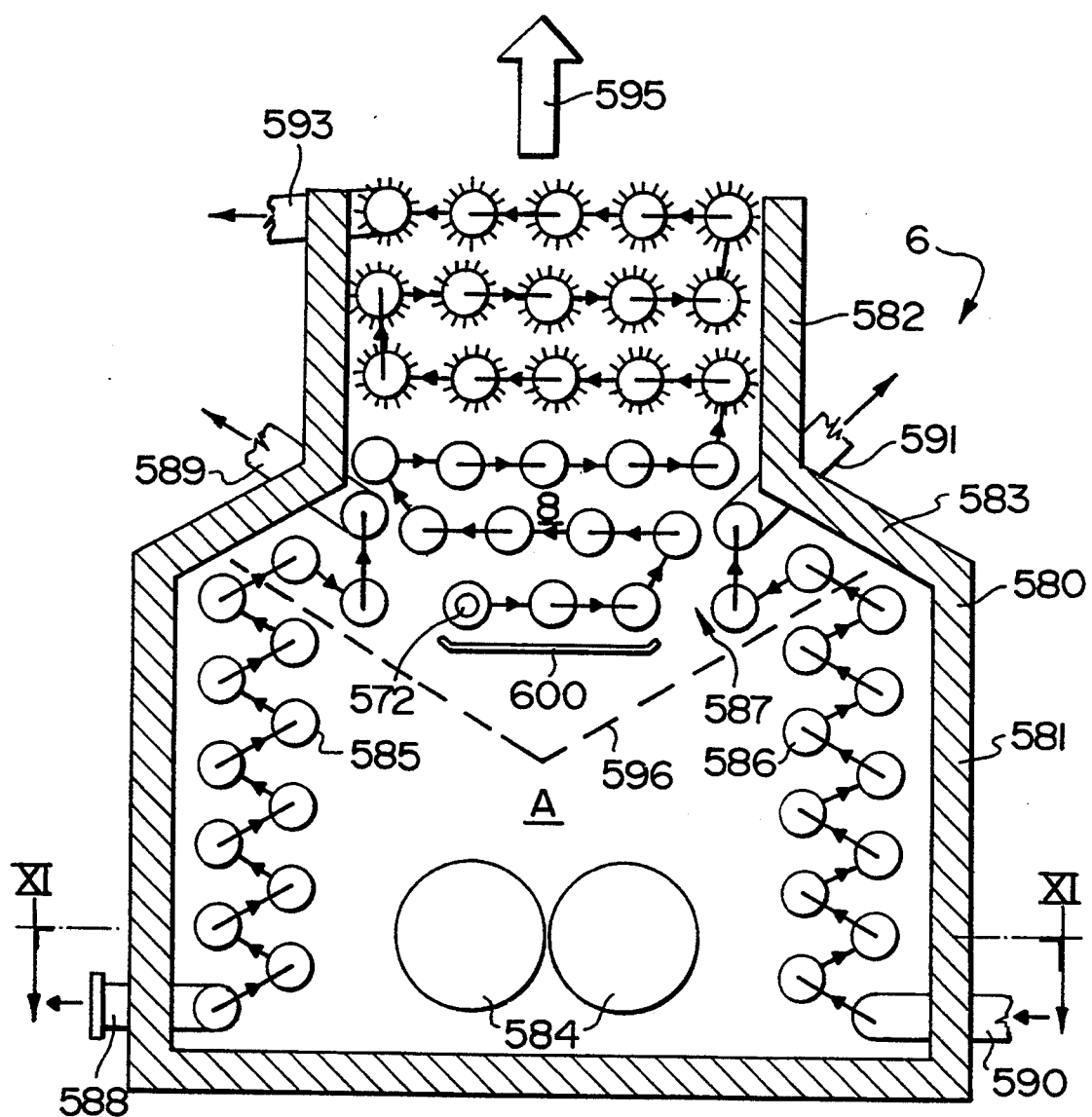
FIG. 10 is a vertical cross-section of a heater used in the apparatus of FIG. 6.
Figure 11:
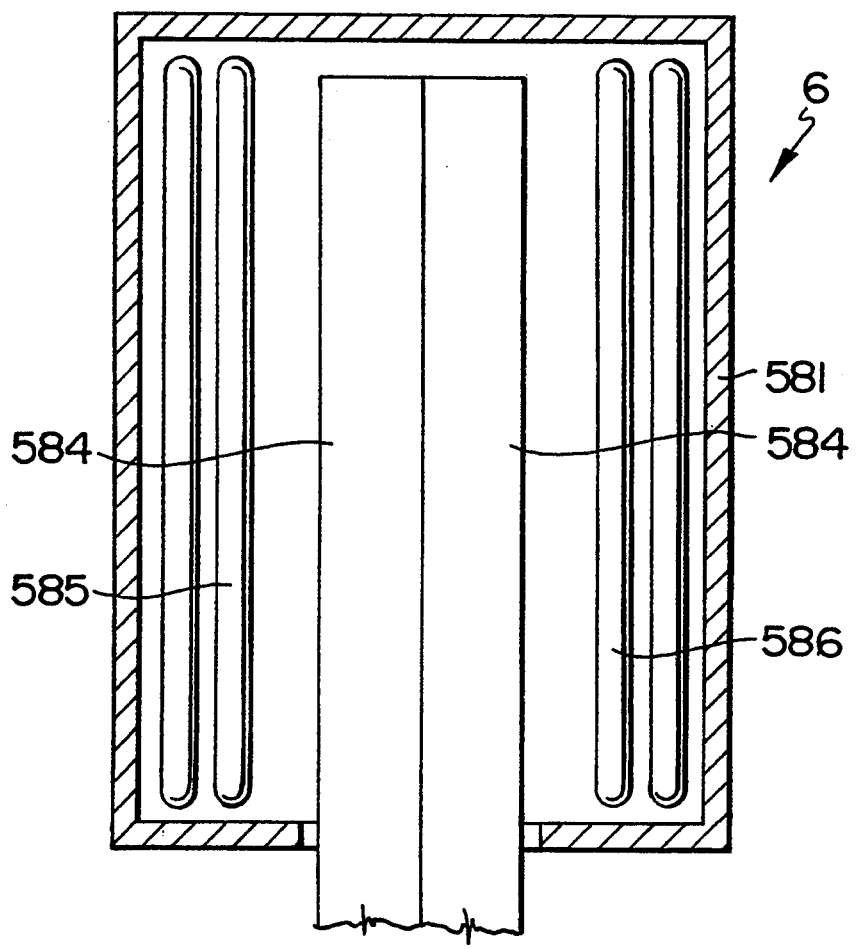
FIG. 11 is a cross-section of the heater of FIG. 10 taken on the line XI—XI.

The preferred heater 6 of FIG. 6, which also could be used in the apparatus of FIG. 1, if desired, is shown in detail in FIGS. 10 and 11. The heater 6 comprises a steel casing 580 lined with refractory material, e.g. firebrick backed with a castable refractory. As shown, the housing has an enlarged body 581 and a narrow neck joined by a sloping shoulder section 583. One or more, and preferably a pair of burners 584 are positioned centrally within the lower part of the body portion 581. These burners may be fired, for example, by natural gas or oil.

Positioned around the walls of the enlarged portion 581 are interconnected tubes forming tube coils 585 and 586. Further interconnected tubes are provided in the shoulder region 583 and the neck region 582 above the burners 584 to form a further coil 587.

Coil 585 receives liquid residue from still 5 via inlet 588 and moves upwardly through the tubes in the direction of the arrows. The liquid then exits the heater via outlet 589 and transported by insulated tubing outside the heater to coil 586 via inlet 590 where again the liquid rises through the coil in the direction of the arrows. The liquid again exits the heater via outlet 591 and are transported outside the heater to reenter via inlet 592 to the coil 587. The liquid rises through the coil in the direction of the arrows and finally exit the heater through outlet 593 for transportation to the mixer 53.

As in the case of heater 6 described in connection with FIGS. 1 to 5, the heater shown in FIGS. 10 and 11 is the sole heat source for the entire apparatus of FIG. 6, and it must again provide heat in such a way that the liquid does not undergo decomposition reactions, which degrade the gas treating chemical, nor generate corrosive conditions which might quickly corrode and destroy the carbon steel tubes used to form coils 585, 586 and 587.

The tubes forming coils 585, 586 and 587 are of such a diameter and total length that, given the capacity of the still recirculation pump 61 and the burners 584, the liquid flows through the tubes so quickly that temperatures in the thin liquid film immediately adjacent to the tube walls do not exceed 400° F., but the liquid residue nevertheless picks up sufficient heat to reach a bulk (centre line) temperature at outlet 593 of about 360° F. Advantageously, the fluid flow through the tubes is at least seven feet per second.

It will also be appreciated that the liquid residue passes completely through the heater in a single pass since the tubing is not divided into two or more parallel flow paths and later recombined. The one-pass flow ensures that there can be no problem of flow distribution between parallel paths and that all points of the tubes receive a positive full flow of circulated liquid residue. This avoids the development of points at which the liquid has a low velocity which could result in overheating and thus decomposition and/or corrosion.

It will also be noted that the circulated liquid residue flows generally co-current to the combustion gases (the latter being indicated by arrow 595). This means that the inlet liquid at its coolest enters the heater via inlet 588 in the radiant combustion zone A of the heater indicated generally by dotted line 596. The liquid residue heated in this way are then circulated to coil 586 while still relatively cool again to be introduced into the radiant heating zone A. The heated liquid residue then pass to coil 587 positioned fully within the convection heating zone B, where heating is less rapid and intense, and they finally exit the heater 6 at the top of the heater via outlet 593 where the combustion gases are at their lowest temperature. This arrangement ensures that the liquid residue, when at its highest bulk temperature, is exposed only to the lowest temperature combustion gases so that the maximum tube wall film temperature is raised by a minimum above the bulk temperature.

In order to reduce the potential for high heat transfer and resulting high film temperature in those tubes at the front of the entrance to the convection section which are fully exposed to the radiant transfer from the combustion zone, a heat resistant baffle 300 (made, for example, of stainless steel) is provided beneath those tubes to prevent them from receiving the full direct radiation from the visible flame.

These features make it possible to construct the tubes of coils 585, 586 and 587 from carbon steel, as stated, because the temperature of the liquid residue never gets so high that corrosion becomes a serious problem.

The use of finned tubes for the top three rows of tubes in the convection section B (as shown) provides the benefits of obtaining high energy efficiency while reducing the exit temperature of the combustion gases to a level where the use of carbon steel without refractory lining for the combustion gas breaching and stack (not shown) becomes both practical and safe.

It will be appreciated that the apparatus of FIG. 6 to 11, and especially the still 5 and heater 6, may be made substantially entirely of carbon steel and that it may be used either to reclaim waste aqueous gas treating solutions or to concentrate them for more economical disposal while producing, as a by-product, water of such purity that it can be discarded in any convenient manner.

What we claim is:

1. A continuous process for reclaiming an impurity-containing waste aqueous solution of a gas treating chemical having a decomposition temperature in such a way that the process can be operated in apparatus made of carbon steel without causing substantial corrosion of said apparatus, which process comprises the steps of:
    (a) heating a feed of said waste aqueous solution to a temperature below said decomposition temperature and subjecting said heated waste solution to a high vacuum of at least 16 inches of mercury in order to produce a vapor comprising water vapor and vaporized gas treating chemical and a liquid residue containing said impurities;
    (b) separating said vapor from said liquid residue;
    (c) heating most of said liquid residue separated from said vapor to a temperature below said decomposition temperature while avoiding localized overheating of said liquid residue to a temperature above said decomposition temperature;
    (d) thoroughly mixing said heated liquid residue with said waste aqueous feed solution to effect said heating of step (a); and
    (e) condensing said vapor to produce a purified solution of said gas treating chemical.

2. A process according to claim 1 wherein said heating of most of said liquid residue in step (c) is carried out by passing said residue through tubes provided in a heater which generates hot combustion gases flowing around said tubes, the liquid residue being conveyed through said heater by said tubes in a single pass in a direction substantially co-current to said combustion gases at a rate of flow high enough to prevent residue in a film contacting inner surfaces of said tubes from exceeding said decomposition temperature.

3. A process according to claim 2 wherein said rate of flow of said liquid residue through said tubes is at least six feet per second.

4. A process according to claim 2 wherein said rate of flow of said liquid through said tubes is seven to ten feet per second.

5. A process according to claim 2 wherein said heater produces radiant heat as well as convected heat carried by said combustion gases, and wherein said tubes are exposed to said radiant heat in a first region where said liquid residue enters said heater but are shielded from said radiant heat in a second region where said liquid residue exits said heater.

6. A process according to claim 1 wherein said heated waste solution is subjected to said high vacuum in step (a) while being forced to flow over a curved surface in order to facilitate said separation of said vapor from said liquid residue in step (b).

7. A process according to claim 6 wherein said curved surface is an upright conical surface tapering downwardly and inwardly and wherein said heated liquid is introduced generally horizontally and tangentially onto said surface at an upper region thereof at such a velocity that the solution flows around said conical surface coating a substantial portion thereof as it is drawn downwardly by gravity.

8. A process according to claim 1 wherein said condensing of said vapor in step (e) is carried out by first condensing said vapor of said gas treating chemical and some water vapor to produce said purified solution of said gas treating chemical and then separately condensing remaining water vapor to produce a liquid water condensate.

9. A process according to claim 8 wherein said first condensation is carried out by passing said vapor upwardly through a vertical wash column provided with internal packing forming an enlarged surface area exposed to said vapor and passing liquid water downwardly over said internal packing, such that vapor reaching an upper region of said column is substantially pure water vapor and liquid reaching a lower region of said column is a concentrated aqueous solution of said gas treating chemical.

10. A process for concentrating a waste impurity-containing aqueous solution of a gas treating chemical having a decomposition temperature in such a way that the process can be operated in apparatus made of carbon steel without causing substantial corrosion of said apparatus, which process comprises the steps of:
(a) heating said waste aqueous solution to a temperature below said decomposition temperature and subjecting said heated waste solution to a high vacuum of at least 16 inches of mercury in order to produce substantially pure water vapor and a liquid residue containing most of said gas treating chemical and said impurities;
(b) separating said water vapor from said liquid residue;
(c) heating a portion of said liquid residue separated from said water vapor to a temperature below said decomposition temperature while avoiding localized overheating of said liquid residue to a temperature above said decomposition temperature;
(d) discharging an unheated portion of said liquid residue as a concentrated impurity-containing aqueous solution of said gas treating chemical;
(e) thoroughly mixing said heated portion of said liquid residue with said waste aqueous feed solution to effect said heating of step (a); and
(f) condensing said water vapor to produce a liquid water condensate.

11. A process according to claim 10 wherein said cooling of said water vapor of step (f) is carried out by first passing said water vapor upwardly through a vertical wash column provided with internal packing forming an enlarged surface area exposed to said vapor and passing liquid water downwardly over said internal packing, such that vapor reaching an upper region of said column is substantially pure water vapor and liquid reaching a lower region of said column contains any gas treating chemical originally contaminating said water vapor; and then condensing said substantially pure water vapor from said upper region.

12. A process according to claim 11 wherein said liquid from said wash column containing said gas treating chemical is added to said unheated portion of said liquid residue discharged in step (d).

13. A process according to claim 11 wherein said liquid from said wash column containing said gas treating chemical is added to said waste aqueous solution to be heated in step (a).

14. A process according to claim 10 wherein said heating of said portion of said liquid residue in step (c) is carried out by passing said residue through tubes provided in a heater which generates hot combustion gases flowing around said tubes, the liquid residue being conveyed through said heater by said tubes in a single pass in a direction substantially co-current to said combustion gases at a rate of flow high enough to prevent residue in a film contacting inner surfaces of said tubes from exceeding said decomposition temperature.

15. A process according to claim 14 wherein said rate of flow of said liquid residue through said tubes is at least six feet per second.

16. A process according to claim 14 wherein said rate of flow of said liquid through said tubes is seven to ten feet per second.

17. A process according to claim 14 wherein said heater produces radiant heat as well as convected heat carried by said combustion gases, and wherein said tubes are exposed to said radiant heat in a first region where said liquid residue enters said heater but are shielded from said radiant heat in a second region where said liquid residue exits said heater.

18. A process according to claim 10 wherein said heated waste solution is subjected to said high vacuum in step (a) while being forced to flow over a curved surface in order to facilitate said separation of said vapor from said liquid residue in step (b).

19. A process according to claim 18 wherein said curved surface is an upright conical surface tapering downwardly and inwardly and wherein said heated liquid is introduced generally horizontally and tangentially onto said surface at an upper region thereof at such a velocity that the solution flows around said conical surface coating a substantial portion thereof as it is drawn downwardly by gravity.

20. A continuous process for reclaiming an aqueous solution of a chemical having a decomposition temperature from a liquid mixture containing said chemical and impurities, comprising:
(a) heating said mixture to a temperature below said decomposition temperature of said chemical in a high vacuum of at least 16 inches of mercury to form a product vapor containing vaporized chemical and a liquid residue containing said impurities;

(b) separating said product vapor from said liquid residue;

(c) heating most of said liquid residue separated from said product vapor to a temperature below said decomposition temperature to produce a heated residue;

(d) thoroughly mixing said heated residue with said mixture to effect heating step (a); and (e) condensing said product vapor separated in step (b) to recover a purified solution of said chemical.

21. A process for concentrating a waste impurity-containing aqueous solution of a chemical, having a decomposition temperature, dissolved in water, comprising:

(a) heating said solution to a temperature below said decomposition temperature of said chemical and subjecting said heated solution to a high vacuum of at least 16 inches of mercury in order to produce substantially pure vapor of said water and a liquid residue containing most of said chemical and said impurities;

(b) separating said water vapor from said liquid residue;

(c) heating a portion of said liquid residue separated from said water vapor to a temperature below said decomposition temperature while avoiding localized overheating of said liquid residue to a temperature above said decomposition temperature;

(d) discharging an unheated portion of said liquid residue as a concentrated impurity-containing solution of said chemical;

(e) thoroughly mixing said heated portion of said liquid residue with said waste solution to effect said heating of step (a); and (f) condensing said water vapor to produce a liquid water condensate.

* * * * *